US011877879B2

(12) United States Patent
Wicklein et al.

(10) Patent No.: US 11,877,879 B2
(45) Date of Patent: Jan. 23, 2024

(54) SYNTHETIC MAMMOGRAM WITH IMPRINTED IMAGE IMPRESSION

(71) Applicant: Siemens Healthcare GmbH, Erlangen (DE)

(72) Inventors: Julia Wicklein, Neunkirchen a. Br. (DE); Wen Man He, Erlangen (DE); Ludwig Ritschl, Erlangen (DE); Ramyar Biniazan, Nuremberg (DE); Stephan Dwars, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 533 days.

(21) Appl. No.: 16/682,388

(22) Filed: Nov. 13, 2019

(65) Prior Publication Data
US 2020/0163638 A1 May 28, 2020

(30) Foreign Application Priority Data

Nov. 23, 2018 (EP) .................................... 18208120
Dec. 20, 2018 (EP) .................................... 18214794

(51) Int. Cl.
*A61B 6/00* (2006.01)
*A61B 6/02* (2006.01)
*A61B 90/00* (2016.01)

(52) U.S. Cl.
CPC .............. *A61B 6/502* (2013.01); *A61B 6/025* (2013.01); *A61B 6/5205* (2013.01); *A61B 6/54* (2013.01); *A61B 90/39* (2016.02); *A61B 2090/3908* (2016.02)

(58) Field of Classification Search
CPC ................................ A61B 6/502; A61B 6/025
See application file for complete search history.

(56) References Cited

U.S. PATENT DOCUMENTS 5,704,355 A * 1/1998 Bridges ................ A61B 5/0507
600/407
9,569,864 B2 2/2017 Abdurahman et al.
2009/0123052 A1 * 5/2009 Ruth ...................... A61B 6/502
382/132

(Continued)

FOREIGN PATENT DOCUMENTS

EP          2998936 B1     4/2017
WO    WO-2016078958 A1    5/2016

OTHER PUBLICATIONS

Zuley, Margarita L et al. "Comparison of two-dimensional synthesized mammograms versus original digital mammograms alone and in combination with tomosynthesis images." Radiology vol. 271,3 (2014): 664-71. doi:10.1148/radiol.13131530. (Year: 2014).*

(Continued)

*Primary Examiner* — Angela M Hoffa
*Assistant Examiner* — Younhee Choi
(74) *Attorney, Agent, or Firm* — Harness, Dickey & Pierce, P.L.C.

(57) ABSTRACT

A method is for generating a synthetic mammogram. In an embodiment, the method incudes acquisition of a plurality of projection data sets at a plurality of projection angles; and generation of at least one synthetic mammogram with an image property essentially equivalent to a conventional full-field digital mammography acquisition based on several projection data sets.

23 Claims, 6 Drawing Sheets

(56) References Cited

U.S. PATENT DOCUMENTS

| | | | | |
|---|---|---|---|---|
| 2014/0093029 | A1* | 4/2014 | Masumoto | A61B 6/502 378/4 |
| 2016/0078645 | A1 | 3/2016 | Abdurahman et al. | |
| 2016/0086356 | A1* | 3/2016 | Abdurahman | A61B 6/032 382/131 |
| 2016/0367210 | A1* | 12/2016 | Gkanatsios | A61B 6/5223 |
| 2017/0011534 | A1* | 1/2017 | Costa | G06T 7/62 |
| 2017/0316588 | A1* | 11/2017 | Homann | G06T 11/008 |
| 2018/0185000 | A1 | 7/2018 | Arai et al. | |
| 2021/0118199 | A1* | 4/2021 | Chui | G16H 50/20 |
| 2022/0015731 | A1* | 1/2022 | Liu | G06T 11/008 |

OTHER PUBLICATIONS

Van Schie et al. "Generating Synthetic Mammograms From Reconstructed Tomosynthesis Volumes." IEEE Trans Med Imaging, vol. 32, 12 (2013): 2322-31. doi: 10.1109/TMI.2013.2281738. (Year: 2013).*

Sickles et al. ACR BI-RADS® Mammography. In: ACR BI-RADS® Atlas, Breast Imaging Reporting and Data System. Reston, VA, American College of Radiology; 2013 (Year: 2013).*

Aguilar et al. Breat Tomosynthesis: A Better Mammography. Mastology, 2018;28(1):51-66. Doi: 10.29289/Z2594539420180000254 (Year: 2018).*

* cited by examiner

SYNTHETIC MAMMOGRAM WITH IMPRINTED IMAGE IMPRESSION

PRIORITY STATEMENT

The present application hereby claims priority under 35 U.S.C. § 119 to European patent application numbers EP 18214794.2 filed Dec. 20, 2018 and EP 18208120.8 filed Nov. 23, 2018, the entire contents of each of which are hereby incorporated herein by reference.

FIELD

Embodiments of the invention generally relate to the generation of a synthetic mammogram with an imprinted image impression.

BACKGROUND

Digital breast tomosynthesis (DBT) enables a three-dimensional imaging of the breast. Several slices in different positions, in particular heights, of the breast are reconstructed from a multiplicity of projection data sets, for example 25. The acquisition of a projection data set takes place at a projection angle. The projection data sets are acquired for different projection angles. The different projection angles can be acquired in particular in a limited angular range of for example 50 degrees.

One major advantage of digital breast tomosynthesis compared to conventional full-field digital mammography (FFDM) is the possibility to resolve overlapping tissue. This is particularly advantageous for the identification of what are known as masses with spiculated lesions in certain slices, which in a full-field digital mammography acquisition can be overlaid with overlapping tissue structures or vessels from other slices and are thus identifiable only with difficulty.

Full-field digital mammography nevertheless has an advantage in terms of the image review speed and the representation of microcalcification clusters. For this reason, clinical protocols currently comprise digital breast tomosynthesis and full-field digital mammography in order to combine the advantages of both imaging techniques. Since a similar patient dose is used in each case for digital breast tomosynthesis and full-field digital mammography, approximately double the dose is required for the combination of both imaging techniques compared to full-field digital mammography alone. It is therefore desirable to calculate a synthetic mammogram from the acquisition data sets or projection data sets of the digital breast tomosynthesis, wherein the additional dose can be avoided and the advantages of the two-dimensional full-field digital mammography are retained. A specific application for a two-dimensional representation of this kind is the comparison with earlier acquisitions. These earlier acquisitions are full-field digital mammography acquisitions from previous screenings or examinations, which have been stored for the affected patient. The object now is to find differences between the current and previous conditions or anomalies and their relative sizes within the breast. For example, the distribution of dense breast tissue or the growth of specific masses can be reviewed and compared. Customers and users can choose between different predefined image impression settings, known as flavors, for the post-processing of the full-field digital mammography acquisition.

The calculation of the synthetic mammogram or of a synthetic projection on the basis of tomosynthesis data sets does however entail a number of technical obstacles. Since the projection data sets are acquired with only a fraction of the dose for a full-field digital mammography acquisition, for example 1/25 of the dose for 25 projections, the contrast-to-noise ratio suffers enormously for each individual projection. Furthermore, a blurring of the information can be expected on account of the movement of the X-ray source. For this reason, the use of a single projection acquisition does not fulfill the requirements for an acquisition with satisfactory quality. Back projections of the reconstructed volume data with an average intensity projection (AIP), which is similar to a physical line integration, also suffers from a blurring of information. This can be attributed to reconstruction artifacts, such as described for example in the publications EP 2 998 936 B1 and U.S. Pat. No. 9,569,864 B2.

A method for generating a combined projection image of a medical inspection object is known from the publication EP 2 998 936 B1.

A method for generating a projection image from tomographic images is known from the publication U.S. Pat. No. 9,569,864 B2.

SUMMARY

The inventors have discovered that a problem is that synthetic mammograms are calculated in a dynamic region which differs from full-field digital mammography and are processed by way of a post-processing step which differs from full-field digital mammography. The difference in the dynamic region results from the calculation methods of the synthetic mammogram.

They have further recognized that until now, therefore, only a single image impression setting or a single image impression has been provided for all users, which differs from the image impression or with regard to at least one image property of a full-field digital mammography acquisition. This makes it significantly more difficult to compare earlier full-field digital mammography acquisitions with current synthetic mammograms, particularly for users with very specific or unique image impression settings of the full-field digital mammography acquisitions.

Embodiments of the invention specifies a method and an apparatus which enable an image impression corresponding to an earlier full-field digital mammography acquisition.

Embodiments of the invention are directed to a method for generating a synthetic mammogram and a mammography system.

At least one embodiment of the application relates to a method for generating a synthetic mammogram having the acquisition and generation steps. A synthetic mammogram can describe in particular a two-dimensional image data set comprising a view of the examination object which corresponds essentially to the conventional full-field digital mammography acquisition. Here, the synthetic mammogram is generated in particular from an essentially three-dimensional data set, in particular several projection data sets. In the acquisition step, a plurality of projection data sets is acquired at a plurality of projection angles. The projection angles lie in a limited angular range. The angular range can lie in the range between 40 and 90 degrees, preferably the angular range corresponds to approximately 50 degrees. The number of project angles can lie in the range between 15 and 40, preferably 25 projections are acquired. The multiplicity of projection data sets can be acquired in particular with an X-ray spectrum. The dose used or the tube current used can be essentially the same for the multiplicity of projection data sets. In the generation step, at least one synthetic mammogram is generated with an image property essentially equivalent to a conventional full-field digital mammography acquisition based on several projection data sets. In the generation step, a selection from the multiplicity of projection data sets or all projection data sets can be used.

At least one embodiment of the application further relates to a mammography system for carrying out a method according to one embodiment of the application, having an acquisition unit and a generation unit. The generation unit can preferably be incorporated in the data processing unit, which can include at least one processor. The mammography system can further comprise a unit for determining an average intensity projection, a unit for intensity adjustment, a unit for gray value distribution adjustment or/and scattered ray correction, a unit for calcification-retaining noise filtering, a unit for determining the maximum intensity projection, a unit for frequency decomposition, a unit for scaling, a recombination unit, and an imprinting unit. The mammography system can advantageously carry out all steps of the method according to the invention. The mammography system is a medical device. Alternatively, other medical devices which are suitable for tomosynthesis methods can also apply the method according to at least one embodiment of the invention.

At least one embodiment of the application also relates to a computer program product with a computer program which can be loaded directly into a memory store of a control device of a mammography system, having program portions in order to carry out all steps of the method according to at least one embodiment of the application when the computer program is executed in the control device of the mammography system.

At least one embodiment of the application also relates to a computer-readable medium, on which program portions that can be read in and executed by a computer unit are stored, in order to carry out all steps of the method according to at least one embodiment of the application when the program portions are executed by the computer unit. The computer unit can preferably be incorporated in the data processing unit or in a processor unit.

At least one embodiment of the application also relates to a method for generating a synthetic mammogram, comprising:
  acquiring a plurality of projection data sets at a plurality of projection angles; and
  generating at least one synthetic mammogram with an image property essentially equivalent to a conventional full-field digital mammography acquisition based on several projection data sets of the plurality of projection data sets acquired.

At least one embodiment of the application also relates to a mammography system, comprising:
  an acquisition unit to acquire a plurality of projection data sets at a plurality of projection angles; and
  a generation unit to generate at least one synthetic mammogram with an image property essentially equivalent to a conventional full-field digital mammography acquisition based on several projection data sets of the plurality of projection data sets acquired.

At least one embodiment of the application also relates to a non-transitory computer program product storing a computer program, directly loadable into a memory of a controller of a mammography system, including program portions to carry out the method of an embodiment when the computer program is executed in the controller of the mammography system.

At least one embodiment of the application also relates to a non-transitory computer-readable medium storing program portions, readable and executable by at least one processor, to carry out the method of an embodiment when the program portions are executed by the at least one processor.

BRIEF DESCRIPTION OF THE DRAWINGS

Example embodiments of the invention are described in greater detail below with reference to drawings, in which.

DETAILED DESCRIPTION OF THE EXAMPLE EMBODIMENTS

Figure 1:
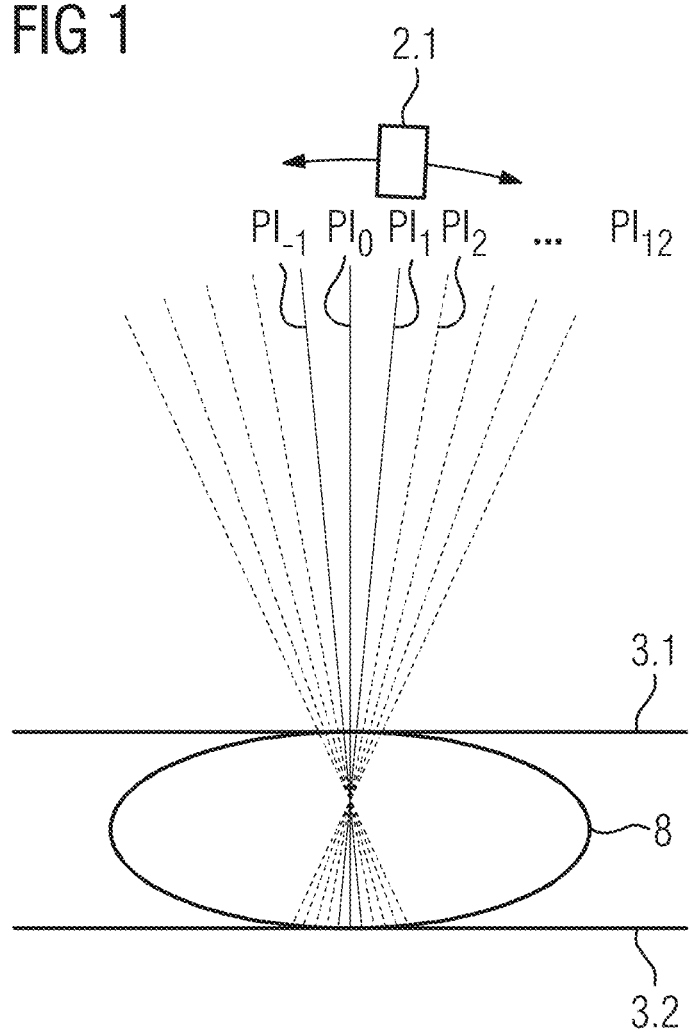
FIG. 1 shows a schematic representation of the mammography system according to the invention in a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the application relates to a method for generating a synthetic mammogram having the acquisition and generation steps. A synthetic mammogram can describe in particular a two-dimensional image data set comprising a view of the examination object which corresponds essentially to the conventional full-field digital mammography acquisition. Here, the synthetic mammogram is generated in particular from an essentially three-dimensional data set, in particular several projection data sets. In the acquisition step, a plurality of projection data sets is acquired at a plurality of projection angles. The projection angles lie in a limited angular range. The angular range can lie in the range between 40 and 90 degrees, preferably the angular range corresponds to approximately 50 degrees. The number of project angles can lie in the range between 15 and 40, preferably 25 projections are acquired. The multiplicity of projection data sets can be acquired in particular with an X-ray spectrum. The dose used or the tube current used can be essentially the same for the multiplicity of projection data sets. In the generation step, at least one synthetic mammogram is generated with an image property essentially equivalent to a conventional full-field digital mammography acquisition based on several projection data sets. In the generation step, a selection from the multiplicity of projection data sets or all projection data sets can be used.

The equivalent image property can result in particular in the image impression of the synthetic mammogram corresponding essentially to the image impression of a conventional full-field digital mammography acquisition. In addition, the dynamic range of the synthetic mammogram can correspond essentially to the dynamic range, the contrast or/and the brightness of a conventional full-field digital mammography acquisition. The image property can comprise the dynamic range, the contrast or the brightness. The equivalent image property can mean that the image property of the synthetic mammogram and the image property of the conventional full-field digital mammography acquisition is essentially the same. The image property can differ for example by a few percent, for example less than 10 percent, preferably less than 5 percent. Advantageously, a comparison of the synthetic mammogram with an earlier conventional full-field digital mammography acquisition can be significantly simplified. For example, the synthetic mammogram can comprise an imprinted, selected predefined image impression setting, known as flavor, wherein the image impression setting is selected such that it corresponds to the predefined image impression setting of the earlier conventional full-field digital mammography acquisition.

In the generation step, a synthetic mammogram is generated or several synthetic mammograms are generated. Preferably at least one synthetic mammogram corresponding to the middle projection data set, especially at a projection angle of 0 degrees, is generated. Here, the middle projection angle can describe in particular the angle at which the central beam of the X-ray source strikes the compressed breast essentially perpendicularly or the upper compression element perpendicularly. Preferably several synthetic mammograms can be generated. A synthetic mammogram can be assigned in each case to a projection angle. A synthetic mammogram can be generated for a projection angle. The maximum number of generated synthetic mammograms can correspond for example to the number of projection angles. Preferably a synthetic mammogram is generated for the projection angle 0 degrees. Furthermore, 2 to the maximum number of acquired projection angles, preferably 10 to 20, particularly preferably 17, synthetic mammograms are generated. The synthetic mammogram can be based in particular on the projection acquisition of the assigned projection angle, for example by using this projection acquisition in the form of an average intensity projection. For example, 17 synthetic mammograms based on 25 projection data sets are generated.

The inventors have recognized that, in order to enable a use of a standard post-processing for full-field digital mammography acquisitions, it is necessary to calculate a novel synthetic mammogram which is equivalent to a detector output. The synthetic mammogram which is equivalent to a detector output has at least one image property which is essentially the same, preferably several such image properties. This synthetic mammogram must therefore ideally lie in the same dynamic range of conventional full-field digital mammography acquisitions. This can be achieved by way of the method according to the invention and the interaction of the steps comprised therein. Following the recombination of the different image components of the different steps to form a synthetic mammogram, it is advantageously possible to use the same post-processing for the synthetic mammogram as for full-field digital mammography acquisition.

The mammography system comprises an X-ray source and an X-ray detector as well as a compression unit. In particular the X-ray source is mounted in a rotatable manner relative to the X-ray detector and the compression unit, enabling different projection angles to be set. The compression unit comprises an upper compression element and a lower compression element, between which the breast of a patient is arranged. In the acquisition step, projection data sets with the breast as the examination object are acquired at different projection angles, while the breast is compressed between the upper and the lower compression element and remains compressed in an essentially unchanged manner during the acquisition step.

Advantageously, the synthetic mammogram can be compared with an earlier full-field digital mammography acquisition. The comparison takes place preferably visually. For example, the synthetic mammogram and the earlier full-field digital mammography acquisition can be displayed side by side. Furthermore, a left-right comparison of synthetic mammograms and the earlier full-field digital mammography acquisitions side by side can be enabled. Advantageously, the combination or the combined acquisition of full-field digital mammography acquisition and digital breast tomosynthesis one after the other can be avoided, enabling the patient dose to be advantageously reduced. Advantageously, the breast density can be acquired particularly easily. Advantageously, the patient dose can be reduced. Advantageously, the time for evaluating the acquisitions can be reduced, as an additional current conventional full-field digital mammography acquisition can be avoided.

According to one embodiment of the invention, this further has the imprinting step, wherein a selected predefined image impression setting is imprinted onto the synthetic mammogram. By way of the imprinting of the selected predefined image impression setting, the image impression of the synthetic mammogram can be adjusted or modified. The image impression setting can be described as what is known as a flavor. The image impression setting can be selected for example from one of the following variants: standard, smoothed, contrast-enhanced, edge-enhanced, or contrast- and edge-enhanced. Advantageously, the image impression can be adjusted by the user.

According to one embodiment of the invention, the predefined image impression setting comprises a multi-frequency adjustment, a lookup table application, or/and a windowing. Advantageously, the image impression can be imprinted in a reproducible manner.

According to one embodiment of the invention, the generation step comprises a determination of an average intensity projection (AIP) based on the multiplicity of projection data sets as the first image component. Preferably a projection data set of a projection angle, in particular corresponding to the assignment of a projection angle to the synthetic mammogram, can be used as the average intensity projection or as the basis for the average intensity projection. In particular, a limited-angle AIP (LARIP) can be used as the average intensity projection. One projection data set or several projection data sets can be selected, on the basis of which the average intensity projection is determined. Advantageously the average intensity projection comprises as the first image component essential information about the examination object in the two-dimensional top view corresponding to the projection angle. However, the average intensity projection alone can hardly satisfy the requirements for a comprehensive assessment of the breast, since it has a relatively high noise on account of the only proportionately used dose.

According to one embodiment of the invention, at least one of the following steps is applied to the average intensity projection: intensity adjustment, gray value distribution adjustment, scattered ray correction, and calcification-retaining noise filter. The average intensity projection can be processed in such a way that the processed average intensity projection can be used as the noisy basis or first image component for the synthetic mammogram. Advantageously the information of this projection can serve as the basis for the synthetic mammogram. Building on the first image component, a synthetic mammogram at least essentially equivalent in terms of quality to a conventional full-field digital mammography acquisition can be generated through the addition of edge information and contrast information of a second image component.

According to one embodiment of the invention, the generation step comprises a determination of a maximum intensity projection (MIP) based on the multiplicity of projection data sets as the second image component. In particular, several projection data sets can be used to determine the maximum intensity projection. In particular, projection data sets which are adjacent to the projection data set assigned to the synthetic mammogram or their projection angles can be used. For example, projection data sets of a suitable angular range about the assigned projection angle can be used. In particular, all projection data sets can be used to determine the maximum intensity projection. Advantageously, edge information and contrast information from several projection data sets can be used as the second image component so that this information can be added to the first image component. Advantageously, the second image component can be used for eliminating noise.

According to one embodiment of the invention, the maximum intensity projection is decomposed into at least two different frequency components. A frequency band decomposition can be performed. According to one embodiment of the invention, the at least two different frequency components comprise high-frequency components and medium-frequency components. The at least two frequency components can be embodied with or without an overlap between one another. The edges can be particularly highlighted by way of the high-frequency components. The contrast or the contrast-to-noise ratio can be improved by way of the medium-frequency components.

According to one embodiment of the invention, the at least two different frequency components are scaled. The at least two different frequency components can be scaled the same or differently. The scaled frequency components can be used as the second image component. The at least two frequency components can advantageously be scaled in a mutually adapted manner. The at least two frequency components can advantageously be scaled in a manner adapted to the first image component.

According to one embodiment of the invention, the first image component and the second image component are recombined to form the synthetic mammogram. The synthetic mammogram can be generated by merging or recombining the first image component and the second image component. It is particularly emphasized that the information of the assigned projection data set in the form of the first image component can advantageously be used together with additional information from several or further projection data sets in the form of the second image component. As a result, the information can advantageously be used for generating the synthetic mammogram on the basis of the patient dose used.

According to one embodiment of the invention, a post-processing step is applied to the synthetic mammogram. The post-processing can comprise an additional filtering, windowing, or generally an adjustment of the representation. Post-processing steps known from conventional full-field digital mammography can advantageously be applied to the synthetic mammogram. In this way, the comparability can be improved further.

According to one embodiment of the invention, the synthetic mammogram is compared with an earlier full-field digital mammography acquisition, in particular with the same flavor. This is advantageously enabled by the synthetic mammogram according to the invention. The comparison is performed in particular visually by a user. In particular, the synthetic mammogram and the earlier full-field digital mammography acquisition, in particular with the same flavor, can be displayed side by side, either for one breast side or both breast sides simultaneously. As a result, the comparison can advantageously be carried out more easily.

According to one embodiment of the invention, the synthetic mammogram can be selected from several generated synthetic mammograms for comparison with an earlier full-field digital mammography acquisition. If several synthetic mammograms are generated, a synthetic mammogram which is most suitable for the comparison can be selected by the user or by way of an algorithm. Advantageously, the comparison of an earlier full-field digital mammography acquisition with a synthetic mammogram of a current acquisition can be simplified. The several synthetic mammograms can be displayed as what are known as rotating mammograms, wherein a three-dimensional view is possible on account of such rotation.

According to one embodiment of the invention, the synthetic mammogram comprises a CAD mark or CAD marks. Computer-aided diagnosis support or image analysis can be provided in the form of what are known as CAD marks (computer-aided diagnosis marks). Lesions, particularly dense breast densities or calcifications can be marked or highlighted by way of machine learning methods, in particular deep learning methods. The CAD mark can be determined in particular within a three-dimensional tomosynthesis volume. The CAD mark can be displayed in the synthetic mammogram which comprises the affected voxel of the CAD mark in the projection. Advantageously, the CAD mark in the synthetic mammogram enables a comprehensive overview of regions within the breast which potentially need to be examined more closely.

At least one embodiment of the application further relates to a mammography system for carrying out a method according to one embodiment of the application, having an acquisition unit and a generation unit. The generation unit can preferably be incorporated in the data processing unit, which can include at least one processor. The mammography system can further comprise a unit for determining an average intensity projection, a unit for intensity adjustment, a unit for gray value distribution adjustment or/and scattered ray correction, a unit for calcification-retaining noise filtering, a unit for determining the maximum intensity projection, a unit for frequency decomposition, a unit for scaling, a recombination unit, and an imprinting unit. The mammography system can advantageously carry out all steps of the method according to the invention. The mammography system is a medical device. Alternatively, other medical devices which are suitable for tomosynthesis methods can also apply the method according to at least one embodiment of the invention.

At least one embodiment of the application also relates to a computer program product with a computer program which can be loaded directly into a memory store of a control device of a mammography system, having program portions in order to carry out all steps of the method according to at least one embodiment of the application when the computer program is executed in the control device of the mammography system.

At least one embodiment of the application also relates to a computer-readable medium, on which program portions that can be read in and executed by a computer unit are stored, in order to carry out all steps of the method according to at least one embodiment of the application when the program portions are executed by the computer unit. The computer unit can preferably be incorporated in the data processing unit or in a processor unit.

FIG. 1 shows an example embodiment of the mammography system according to the invention in a first embodiment. A plurality of projection data sets is acquired at a plurality of projection angles PI-1, 0, 1, 2, . . . , 12. Here, the X-ray source 2.1 is moved in particular along a radius about a point in the breast 8, wherein a projection data set is acquired at each of the projection angles PI-1, 0, 1, 2, . . . , 12. During the acquisition, the breast 8 of a patient as the examination object is arranged between an upper compression element 3.1 and a lower compression element 3.2.

Figure 2:
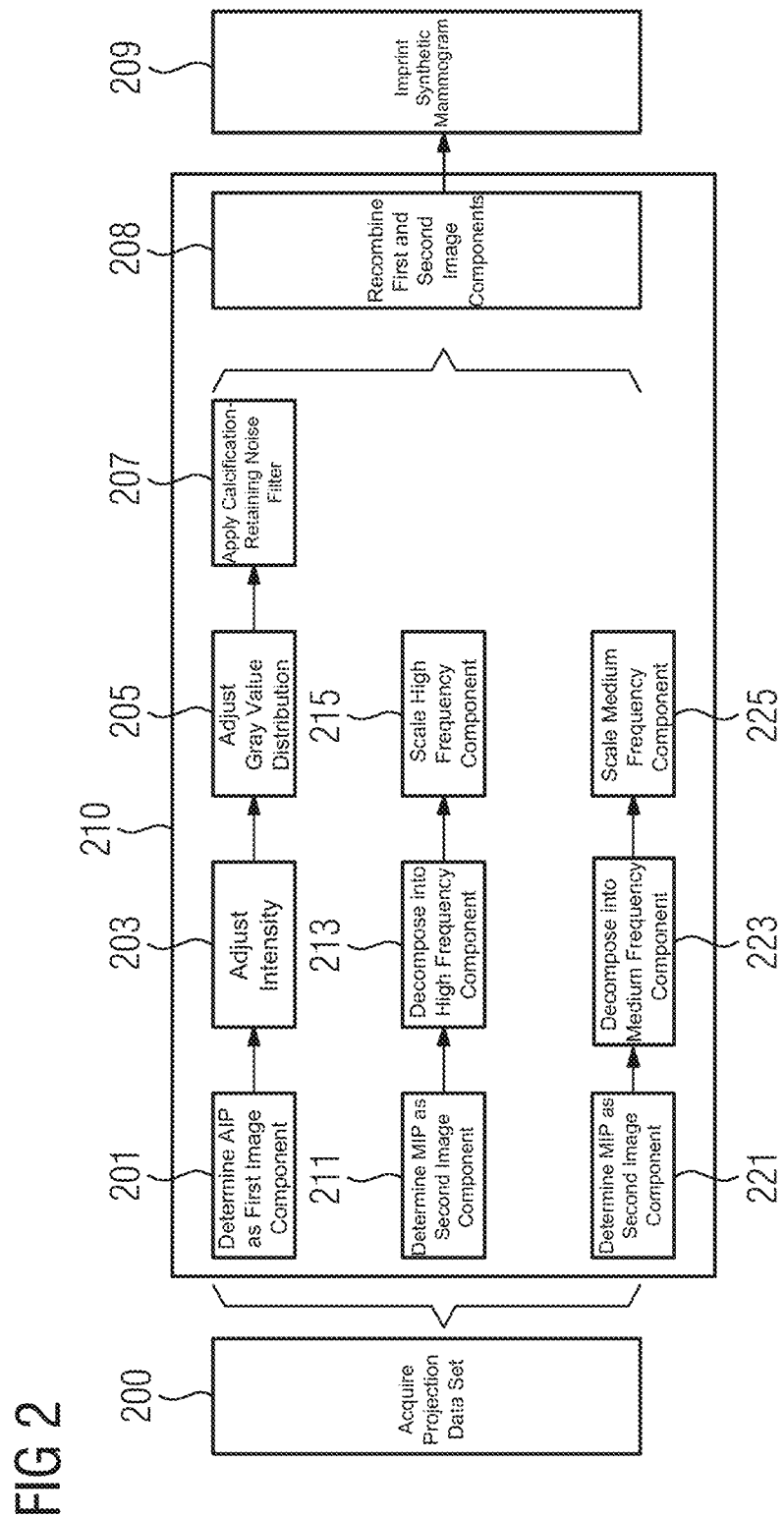
FIG. 2 shows a schematic representation of the method according to an embodiment of the invention.

FIG. 2 shows an example embodiment of the method according to the invention for generating a synthetic mammogram having the acquisition step 200 and the generation step 210. FIG. 2 shows in particular a preferred sequence of the steps. In the acquisition step, a plurality of projection data sets is acquired at a plurality of projection angles. In the generation step, at least one synthetic mammogram is generated with image properties essentially equivalent to a conventional full-field digital mammography acquisition based on several projection data sets. In a particular embodiment, several synthetic mammograms are generated for different projection angles.

In step 201, an average intensity projection (AIP) is determined on the basis of the multiplicity of projection data sets as the first image component. The average projection corresponds in particular to one projection, particularly preferably to the middle projection PI0.

If several synthetic mammograms are generated, then several projections are used in each case as the average projection, so that a synthetic mammogram is generated for each of these projections. The maximum number of generated synthetic mammograms can correspond to the total number of projections. One synthetic mammogram can preferably be generated in each case for 17 out of 25 projections, for example.

At least one of the following steps is applied to the average intensity projection: intensity adjustment 203, gray value distribution adjustment 205 or/and scattered ray correction, and calcification-retaining noise filter 207.

The generation step comprises a determination 211, 221 of a maximum intensity projection (MIP) based on the multiplicity of projection data sets as the second image component. The maximum intensity projection is decomposed into at least two different frequency components in step 213 or 223. The at least two different frequency components comprise high-frequency components in step 213 and medium-frequency components in step 223. The at least two different frequency components are scaled in steps 215, 225.

In the recombination step 208, the first image component and the second image component are recombined to form the synthetic mammogram. The synthetic mammogram has image properties essentially equivalent to a conventional full-field digital mammography acquisition, wherein an imprinting step 209 can comprise a predefined image impression setting by way of a multi-frequency adjustment, a lookup table application, or/and a windowing. In addition, a further post-processing step can be applied to the synthetic mammogram.

Figure 3:
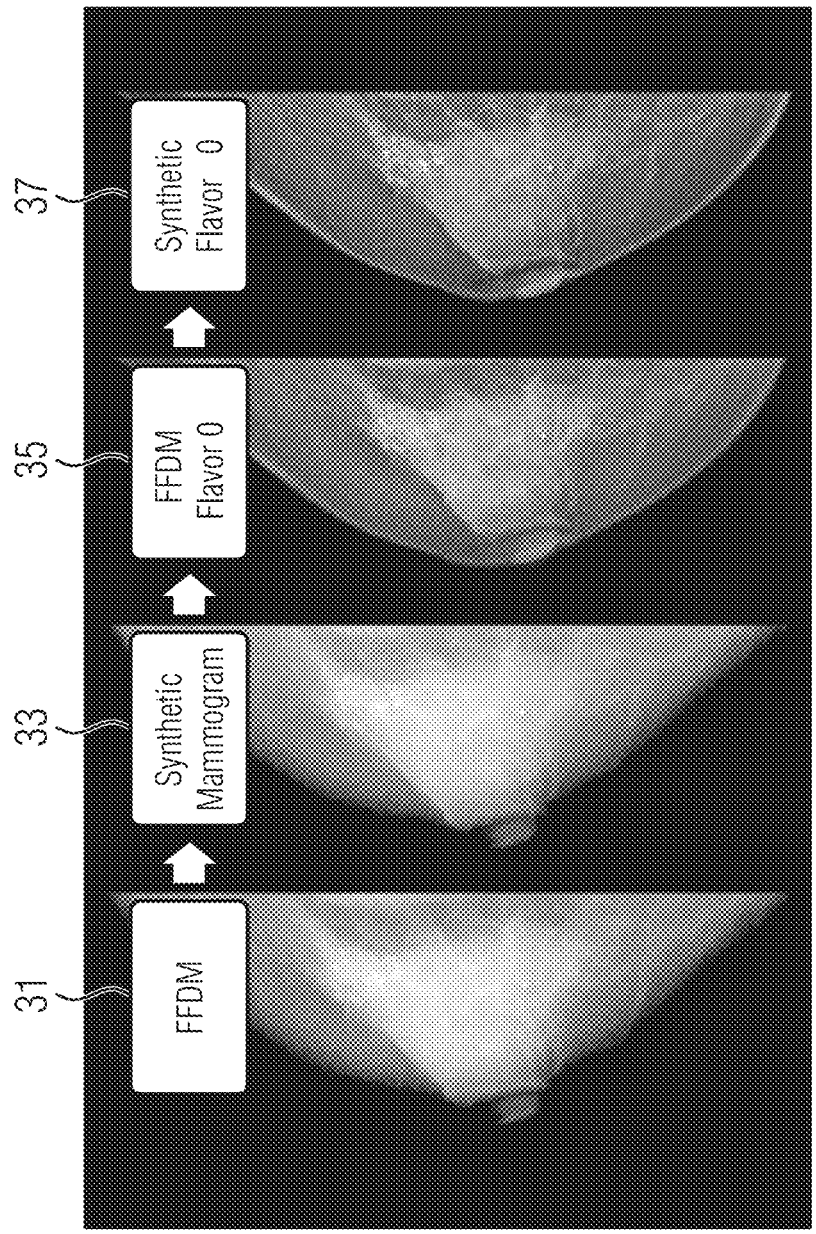
FIG. 3 shows a schematic representation of the synthetic mammograms according to the invention set against conventional full-field digital mammography acquisitions, each with a selected predefined image impression setting, in a first embodiment.

FIG. 3 shows an example embodiment of the synthetic mammograms according to the invention set against conventional full-field digital mammography acquisitions, each with a selected predefined image impression setting, in a first embodiment. The representation 31 shows a conventional full-field digital mammography acquisition without a predefined image impression setting. The representation 33 shows a synthetic mammogram with image properties essentially equivalent to a conventional full-field digital mammography acquisition without a predefined image impression setting. The representation 35 shows a conventional full-field digital mammography acquisition with a predefined image impression setting of the first embodiment, in particular what is known as the flavor 0. The representation 37 shows a synthetic mammogram with a predefined image impression setting of the first embodiment, in particular what is known as the flavor 0.

Figure 4:
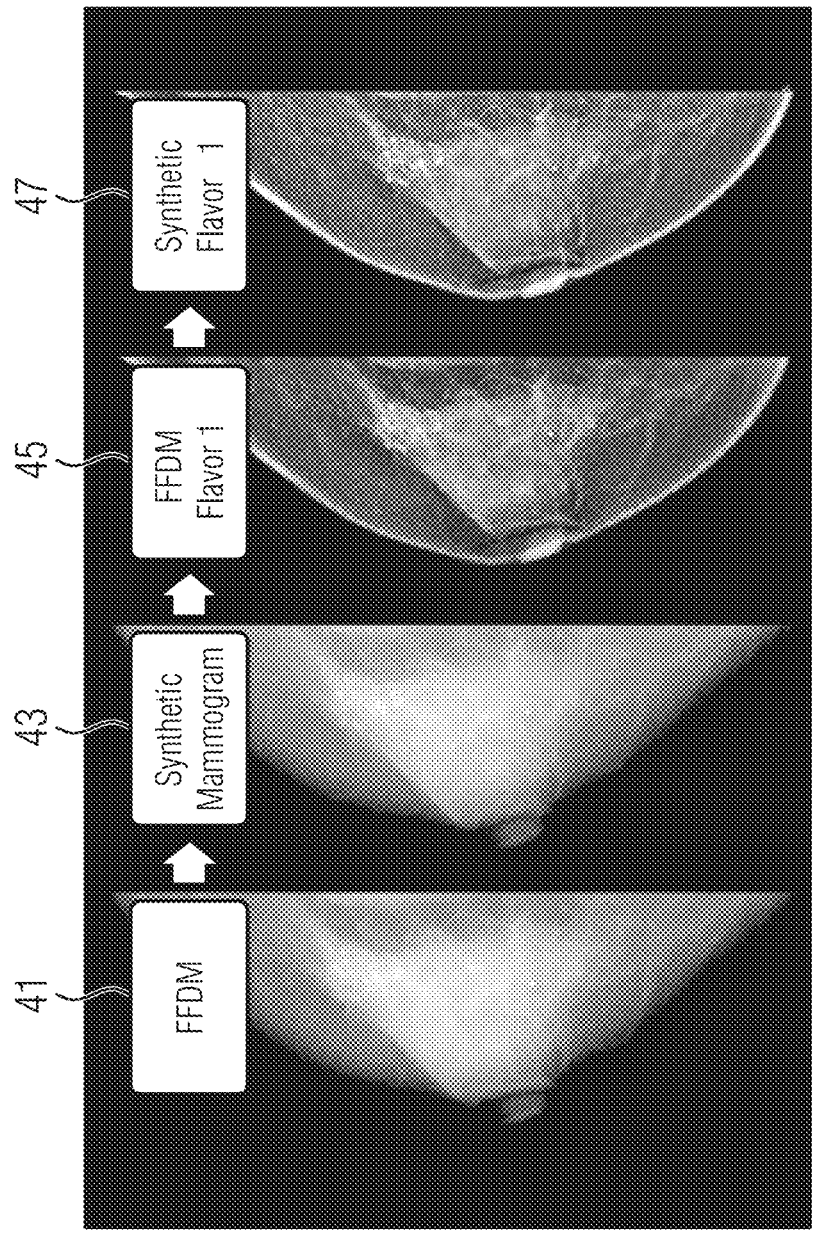
FIG. 4 shows a schematic representation of the synthetic mammograms according to the invention set against conventional full-field digital mammography acquisitions, each with a selected predefined image impression setting, in a second embodiment.

FIG. 4 shows an example embodiment of the synthetic mammograms according to the invention set against conventional full-field digital mammography acquisitions, each with a selected predefined image impression setting, in a second embodiment. The representation 41 shows a conventional full-field digital mammography acquisition without a predefined image impression setting. The representation 43 shows a synthetic mammogram with image properties essentially equivalent to a conventional full-field digital mammography acquisition without a predefined image impression setting. The representation 45 shows a conventional full-field digital mammography acquisition with a predefined image impression setting of the second embodiment, in particular what is known as the flavor 1. The representation 47 shows a synthetic mammogram with a predefined image impression setting of the second embodiment, in particular what is known as the flavor 1.

Figure 5:
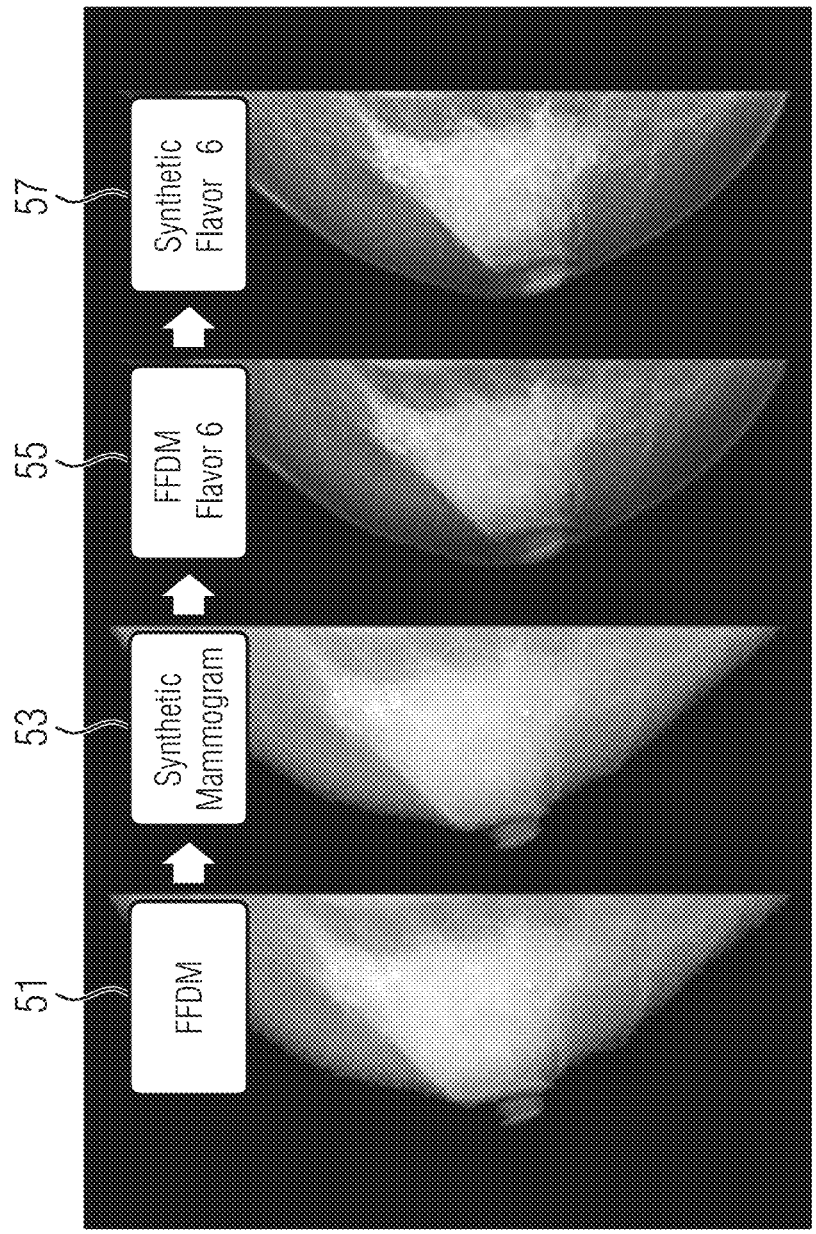
FIG. 5 shows a schematic representation of the synthetic mammograms according to the invention set against conventional full-field digital mammography acquisitions, each with a selected predefined image impression setting, in a third embodiment.

FIG. 5 shows an example embodiment of the synthetic mammograms according to the invention set against conventional full-field digital mammography acquisitions, each with a selected predefined image impression setting, in a third embodiment. The representation 51 shows a conventional full-field digital mammography acquisition without a predefined image impression setting. The representation 53 shows a synthetic mammogram with image properties essentially equivalent to a conventional full-field digital mammography acquisition without a predefined image impression setting. The representation 55 shows a conventional full-field digital mammography acquisition with a predefined image impression setting of the third embodiment, in particular what is known as the flavor 6. The representation 57 shows a synthetic mammogram with a predefined image impression setting of the third embodiment, in particular what is known as the flavor 6.

Figure 6:
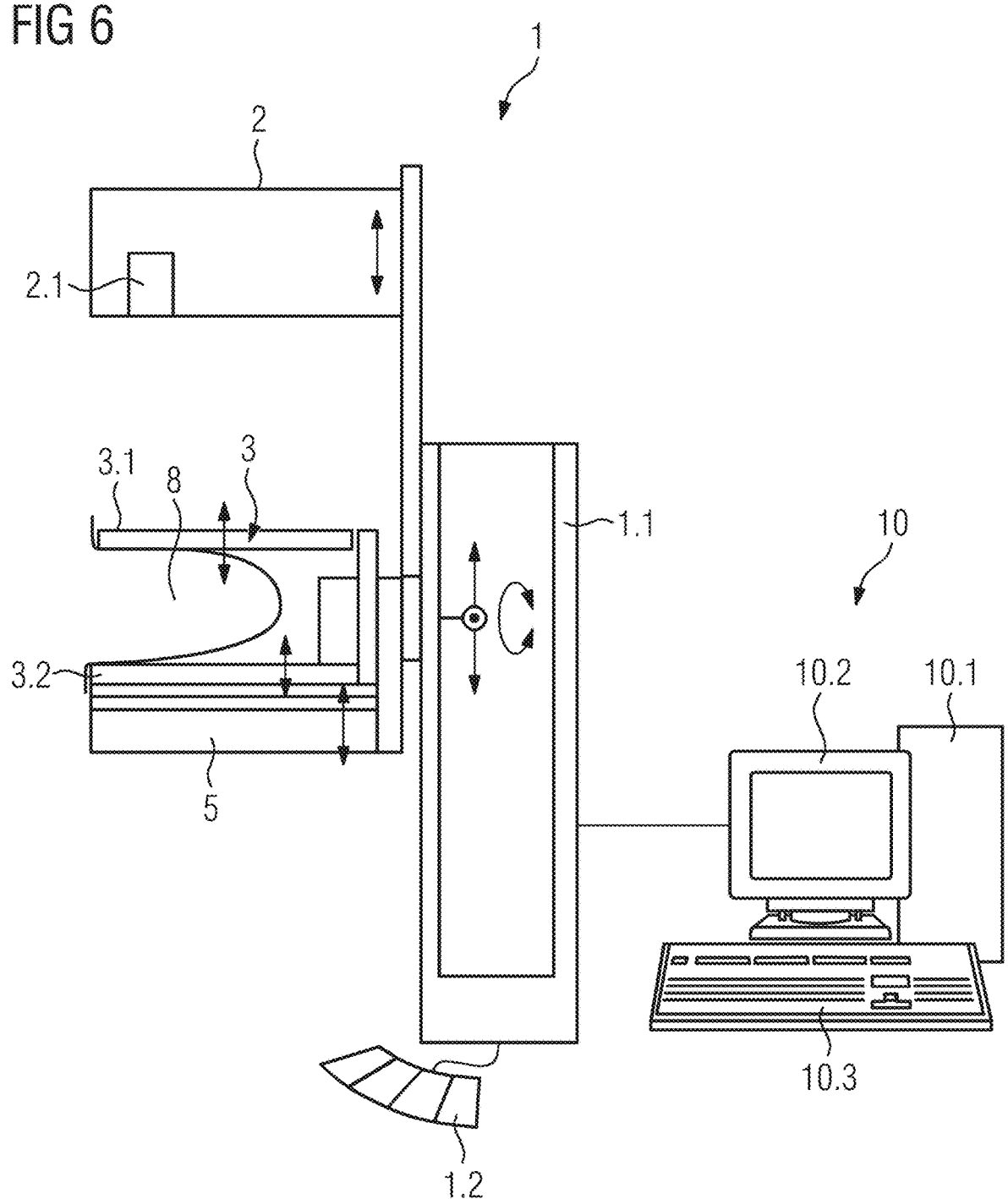
FIG. 6 shows a schematic representation of the mammography system according to the invention in a second embodiment.

FIG. 6 shows an example embodiment of the mammography system 1 according to the invention in a second embodiment. The mammography system 1 comprises a stand 1.1, on which the X-ray housing 2 having the X-ray source 2.1 and the X-ray detector 5 are arranged together with a compression unit 3. The X-ray housing 2 in particular is mounted on the stand 1.1 in a rotatable manner relative to the stand 1.1 and the X-ray detector 5 as well as the compression unit 3. The compression unit 3 comprises an upper compression element 3.1 and a lower compression element 3.2, between which the breast 8 of a patient is arranged. The mammography system 1 is connected to a data processing unit 10. The data processing unit 10 comprises at least a processor unit 10.1, a visualization unit 10.2 and an input unit 10.3. The mammography system 1 can be controlled at least partially by way of a foot switch 1.2.

Although the invention has been illustrated in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating at least one synthetic mammogram, the method comprising:
    acquiring a plurality of projection data sets at a plurality of projection angles;
    generating the at least one synthetic mammogram, the at least one synthetic mammogram having an image property essentially equivalent to a conventional full-field digital mammography acquisition, the image property being at least one of a dynamic range, a contrast or a brightness, the generating including selecting a projection data set from among the plurality of projection data sets as an average intensity projection, and the generating being based on the average intensity projection and at least one projection data set from among the plurality of projection data sets; and
    imprinting a selected image impression setting onto the at least one synthetic mammogram, the selected image impression being based on an image impression of the conventional full-field digital mammography acquisition.

2. The method of claim 1, wherein the selected image impression setting includes at least one of a multi-frequency adjustment, a lookup table application, or a windowing.

3. The method of claim 2, further comprising:
    applying at least one of an intensity adjustment, a gray value distribution adjustment, a scattered ray correction, or a calcification-retaining noise filter to the average intensity projection.

4. The method of claim 1, wherein the average intensity projection is a first image component.

5. The method of claim 4, wherein the generating further comprises:
    applying at least one of an intensity adjustment, a gray value distribution adjustment, a scattered ray correction, or a calcification-retaining noise filter to the average intensity projection.

6. The method of claim 4, wherein the generating further comprises:
determining, as a second image component, a maximum intensity projection based on the plurality of projection data sets.

7. The method of claim 6, wherein the generating further comprises:
recombining the first image component and the second image component to form the at least one synthetic mammogram.

8. The method of claim 6, wherein the generating further comprises:
decomposing the maximum intensity projection into at least two different frequency components.

9. The method of claim 8, wherein the at least two different frequency components include high-frequency components and medium-frequency components.

10. The method of claim 9, wherein the generating comprises:
scaling at least two different frequency components from among the at least two different frequency components.

11. The method of claim 1, wherein the generating comprises:
determining, as an image component, a maximum intensity projection based on the plurality of projection data sets.

12. The method of claim 11, wherein the generating further comprises:
decomposing the maximum intensity projection into at least two different frequency components.

13. The method of claim 12, wherein the at least two different frequency components include high-frequency components and medium-frequency components.

14. The method of claim 13, wherein the generating further comprises:
scaling at least two different frequency components from among the at least two different frequency components.

15. The method of claim 1, further comprising:
applying a post-processing step to the at least one synthetic mammogram.

16. The method of claim 1, further comprising:
comparing the at least one synthetic mammogram with an earlier full-field digital mammography acquisition.

17. The method of claim 16, further comprising:
selecting a synthetic mammogram from the at least one synthetic mammogram for comparison with the earlier full-field digital mammography acquisition.

18. The method of claim 1, wherein the at least one synthetic mammogram comprises CAD marks.

19. A device for generating at least one synthetic mammogram, the device comprising:
one or more processors; and
a memory storing computer-executable instructions that, when executed, cause the one or more processors to perform the method of claim 1.

20. A non-transitory computer-readable medium storing program portions, readable and executable by at least one processor, to carry out the method of claim 1 when the program portions are executed by the at least one processor.

21. A mammography system, comprising:
an acquisition unit configured to acquire a plurality of projection data sets at a plurality of projection angles; and
a generation unit configured to
select a projection data set from among the plurality of projection data sets as an average intensity projection,
generate at least one synthetic mammogram based on the average intensity projection and at least one projection data set from among the plurality of projection data sets, the at least one synthetic mammogram having an image property essentially equivalent to a conventional full-field digital mammography acquisition, the image property being at least one of a dynamic range, a contrast or a brightness, and
imprinting a selected image impression setting onto the at least one synthetic mammogram, the selected image impression being based on an image impression of the conventional full-field digital mammography acquisition.

22. A method for generating at least one synthetic mammogram, the method comprising:
acquiring a plurality of projection data sets at a plurality of projection angles; and
generating the at least one synthetic mammogram, the at least one synthetic mammogram having an image property essentially equivalent to a conventional full-field digital mammography, the image property being at least one of a dynamic range, a contrast, or a brightness, the generating including
determining a maximum intensity projection based on the plurality of projection data sets, and
decomposing the maximum intensity projection into at least two different frequency components, and wherein
the generating is based on the at least two different frequency components and at least one projection data set from among the plurality of projection data sets.

23. The method of claim 22, wherein the generating includes combining the at least two different frequency components.

* * * * *